(12) United States Patent
D'Agostino et al.

(10) Patent No.: US 8,167,895 B2
(45) Date of Patent: May 1, 2012

(54) ANASTOMOSIS COMPOSITE GASKET (75) Inventors: William L. D'Agostino, Mt. Carmel, CT (US); Michael Bettuchi, Middletown, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 0 days.

(21) Appl. No.: 13/080,966

(22) Filed: Apr. 6, 2011

(65) Prior Publication Data
US 2011/0184444 A1 Jul. 28, 2011

Related U.S. Application Data (62) Division of application No. 11/080,854, filed on Mar. 15, 2005, now Pat. No. 7,942,890.

(51) Int. Cl.
*A61B 17/10* (2006.01)
*A61B 17/08* (2006.01)
*A61B 17/04* (2006.01)

(52) U.S. Cl. ..... 606/139; 606/151; 606/153; 227/175.1; 227/180.1

(58) Field of Classification Search .................. 606/139, 606/151–153, 213–215, 219, 142; 227/175.1, 227/180.1
See application file for complete search history.

(56) References Cited

U.S. PATENT DOCUMENTS

| 3,054,406 | A | | 9/1962 | Usher |
| 3,124,136 | A | | 3/1964 | Usher |
| 4,297,995 | A | | 11/1981 | Golub ........................... 604/304 |
| 4,347,847 | A | | 9/1982 | Usher |
| 4,354,628 | A | | 10/1982 | Green |
| 4,452,245 | A | | 6/1984 | Usher |
| 4,605,730 | A | | 8/1986 | Shalaby et al. |
| 4,655,221 | A | | 4/1987 | Devereux |
| 4,665,917 | A | * | 5/1987 | Clanton et al. ................ 606/153 |
| 4,834,090 | A | | 5/1989 | Moore |
| 4,838,884 | A | | 6/1989 | Dumican et al. |
| 4,917,114 | A | * | 4/1990 | Green et al. ................ 227/179.1 |
| 4,930,674 | A | | 6/1990 | Barak |
| 5,002,551 | A | | 3/1991 | Linsky et al. |
| 5,014,899 | A | | 5/1991 | Presty et al. |
| 5,040,715 | A | | 8/1991 | Green et al. |
| 5,065,929 | A | | 11/1991 | Schulze et al. |
| 5,205,459 | A | | 4/1993 | Brinkerhoff et al. |
| 5,250,058 | A | * | 10/1993 | Miller et al. .................. 606/154 |
| 5,263,629 | A | | 11/1993 | Trumbull et al. |
| 5,314,471 | A | | 5/1994 | Brauker et al. |
| 5,344,454 | A | | 9/1994 | Clarke et al. |

(Continued)

FOREIGN PATENT DOCUMENTS
DE     1 99 24 311 A1    11/2000
(Continued)

OTHER PUBLICATIONS

European Search Report (EP 06 00 4598).
(Continued)

*Primary Examiner* — Corrine M McDermott
*Assistant Examiner* — Dianne Dornbusch (57) ABSTRACT

The present disclosure provides structures and/or gaskets for deposition between adjacent intestinal sections in an anastomosis procedure. The structure possesses at least an inner ring of a first material, and a middle ring of a second material. The first material and the second material include a wound treatment material consisting of at least one of an adhesive, a sealant and/or a medicament. The first material is different from the second material.

15 Claims, 4 Drawing Sheets

U.S. PATENT DOCUMENTS

| | | | |
|---|---|---|---|
| 5,392,979 A | 2/1995 | Green et al. |
| 5,397,324 A | 3/1995 | Carroll et al. |
| 5,425,745 A | 6/1995 | Green et al. |
| 5,441,193 A | 8/1995 | Gravener |
| 5,441,507 A | 8/1995 | Wilk et al. |
| 5,468,253 A | 11/1995 | Bezwada et al. |
| 5,503,638 A | 4/1996 | Cooper et al. |
| 5,542,594 A | 8/1996 | McKean et al. |
| 5,549,628 A | 8/1996 | Cooper et al. |
| 5,575,803 A | 11/1996 | Cooper et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,833,695 A | 11/1998 | Yoon |
| 5,843,096 A | 12/1998 | Igaki et al. |
| 5,895,412 A | 4/1999 | Tucker |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov et al. |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,099,551 A | 8/2000 | Gabbay |
| 6,149,667 A | 11/2000 | Hovland et al. |
| 6,155,265 A | 12/2000 | Hammerslag |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,436,030 B2 | 8/2002 | Rehil |
| 6,454,780 B1 | 9/2002 | Wallace |
| 6,461,368 B2 | 10/2002 | Fogarty et al. |
| 6,503,257 B2 | 1/2003 | Grant et al. |
| 6,503,259 B2 * | 1/2003 | Huxel et al. ............ 606/153 |
| 6,514,283 B2 | 2/2003 | DiMatteo et al. |
| 6,517,566 B1 | 2/2003 | Hovland et al. |
| 6,551,356 B2 | 4/2003 | Rousseau |
| 6,592,597 B2 | 7/2003 | Grant et al. |
| 6,638,285 B2 | 10/2003 | Gabbay |
| 6,652,594 B2 | 11/2003 | Francis et al. |
| 6,656,193 B2 | 12/2003 | Grant et al. |
| 6,669,735 B1 | 12/2003 | Pelissier |
| 6,677,258 B2 | 1/2004 | Carroll et al. |
| 6,685,714 B2 | 2/2004 | Rousseau |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,773,458 B1 | 8/2004 | Brauker et al. |
| 6,927,315 B1 | 8/2005 | Heinecke et al. |
| 7,128,748 B2 * | 10/2006 | Mooradian et al. ......... 606/151 |
| 7,147,138 B2 | 12/2006 | Shelton, IV |
| 7,434,717 B2 | 10/2008 | Shelton, IV et al. |
| 7,438,209 B1 | 10/2008 | Hess et al. |
| 7,547,312 B2 * | 6/2009 | Bauman et al. ............. 606/151 |
| 7,559,937 B2 | 7/2009 | de la Torre et al. |
| 7,604,151 B2 | 10/2009 | Hess et al. |
| 7,665,646 B2 | 2/2010 | Prommersberger |
| 7,744,627 B2 * | 6/2010 | Orban et al. ................ 606/215 |
| 7,793,813 B2 | 9/2010 | Bettuchi |
| 7,823,592 B2 | 11/2010 | Bettuchi et al. |
| 7,845,533 B2 | 12/2010 | Marczyk et al. |
| 7,845,536 B2 | 12/2010 | Viola et al. |
| 7,909,224 B2 | 3/2011 | Prommersberger |
| 2002/0016626 A1 | 2/2002 | DiMatteo et al. |
| 2002/0019187 A1 | 2/2002 | Carroll et al. |
| 2002/0052622 A1 | 5/2002 | Rousseau |
| 2002/0091397 A1 | 7/2002 | Chen |
| 2002/0133236 A1 | 9/2002 | Rousseau |
| 2002/0138152 A1 | 9/2002 | Francis et al. |
| 2002/0151911 A1 | 10/2002 | Gabbay |
| 2002/0165559 A1 | 11/2002 | Grant et al. |
| 2002/0165562 A1 | 11/2002 | Grant et al. |
| 2002/0165563 A1 | 11/2002 | Grant et al. |
| 2002/0177859 A1 | 11/2002 | Monassevitch et al. |
| 2003/0065345 A1 | 4/2003 | Weadock |
| 2003/0065346 A1 | 4/2003 | Evens et al. |
| 2003/0083676 A1 | 5/2003 | Wallace |
| 2003/0088256 A1 | 5/2003 | Conston et al. |
| 2003/0105510 A1 | 6/2003 | DiMatteo et al. |
| 2003/0114866 A1 | 6/2003 | Ulmsten et al. |
| 2003/0120284 A1 | 6/2003 | Palacios |
| 2003/0167064 A1 | 9/2003 | Whayne |
| 2003/0181927 A1 | 9/2003 | Wallace |
| 2003/0183671 A1 | 10/2003 | Mooradian et al. |
| 2003/0208231 A1 | 11/2003 | Williamson, IV et al. |
| 2004/0034377 A1 | 2/2004 | Sharkawy et al. |
| 2004/0092960 A1 | 5/2004 | Abrams et al. |
| 2004/0093029 A1 | 5/2004 | Zubik et al. |
| 2004/0107006 A1 | 6/2004 | Francis et al. |
| 2004/0116945 A1 | 6/2004 | Sharkawy et al. |
| 2004/0142621 A1 | 7/2004 | Carroll et al. |
| 2004/0172048 A1 | 9/2004 | Browning |
| 2004/0209059 A1 | 10/2004 | Foss |
| 2004/0215214 A1 | 10/2004 | Crews et al. |
| 2004/0215219 A1 | 10/2004 | Eldridge et al. |
| 2004/0215221 A1 | 10/2004 | Suyker et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021026 A1 | 1/2005 | Baily |
| 2005/0021053 A1 | 1/2005 | Heinrich |
| 2005/0021085 A1 | 1/2005 | Abrams et al. |
| 2005/0059996 A1 * | 3/2005 | Bauman et al. ............. 606/215 |
| 2005/0059997 A1 * | 3/2005 | Bauman et al. ............. 606/219 |
| 2005/0070929 A1 | 3/2005 | Dalessandro et al. |
| 2005/0118435 A1 | 6/2005 | DeLucia et al. |
| 2005/0228446 A1 * | 10/2005 | Mooradian et al. ........... 606/215 |
| 2005/0245965 A1 * | 11/2005 | Orban, III et al. ............ 606/214 |
| 2006/0004407 A1 | 1/2006 | Hiles et al. |
| 2006/0085034 A1 | 4/2006 | Bettuchi |
| 2006/0135992 A1 | 6/2006 | Bettuchi et al. |
| 2006/0173470 A1 | 8/2006 | Oray et al. |
| 2006/0178683 A1 | 8/2006 | Shimoji et al. |
| 2006/0212050 A1 | 9/2006 | D'Agostino et al. |
| 2006/0271104 A1 | 11/2006 | Viola et al. |
| 2007/0034669 A1 | 2/2007 | de la Torre et al. |
| 2007/0049953 A2 | 3/2007 | Shimoji et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0246505 A1 | 10/2007 | Pace-Floridia et al. |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |

| | | | |
|---|---|---|---|
| 2008/0169331 A1 | 7/2008 | Shelton et al. | |
| 2008/0169332 A1 | 7/2008 | Shelton et al. | |
| 2008/0169333 A1 | 7/2008 | Shelton et al. | |
| 2008/0290134 A1 | 11/2008 | Bettuchi et al. | |
| 2008/0308608 A1 | 12/2008 | Prommersberger | |
| 2008/0314960 A1 | 12/2008 | Marczyk et al. | |
| 2009/0001121 A1 | 1/2009 | Hess et al. | |
| 2009/0001122 A1 | 1/2009 | Prommersberger et al. | |
| 2009/0001123 A1 | 1/2009 | Morgan et al. | |
| 2009/0001124 A1 | 1/2009 | Hess et al. | |
| 2009/0001125 A1 | 1/2009 | Hess et al. | |
| 2009/0001126 A1 | 1/2009 | Hess et al. | |
| 2009/0001128 A1 | 1/2009 | Weisenburgh, II et al. | |
| 2009/0001130 A1 | 1/2009 | Hess et al. | |
| 2009/0005808 A1 | 1/2009 | Hess et al. | |
| 2009/0030452 A1 | 1/2009 | Bauman et al. | |
| 2009/0043334 A1 | 2/2009 | Bauman et al. | |
| 2009/0078739 A1 | 3/2009 | Viola | |
| 2009/0095791 A1 | 4/2009 | Bauman et al. | |
| 2009/0095792 A1 | 4/2009 | Bettuchi | |
| 2009/0120994 A1 | 5/2009 | Murray et al. | |
| 2009/0134200 A1 | 5/2009 | Tarinelli et al. | |
| 2009/0206125 A1 | 8/2009 | Huitema et al. | |
| 2009/0206126 A1 | 8/2009 | Huitema et al. | |
| 2009/0206139 A1 | 8/2009 | Hall et al. | |
| 2009/0206141 A1 | 8/2009 | Huitema et al. | |
| 2009/0206142 A1 | 8/2009 | Huitema et al. | |
| 2009/0206143 A1 | 8/2009 | Huitema et al. | |
| 2009/0218384 A1 | 9/2009 | Aranyi | |
| 2009/0277947 A1 | 11/2009 | Viola | |
| 2009/0287230 A1 | 11/2009 | D'Agostino et al. | |
| 2010/0012704 A1 | 1/2010 | Tarinelli Racenet et al. | |
| 2010/0065606 A1 | 3/2010 | Stopek | |
| 2010/0065607 A1 | 3/2010 | Orban, III et al. | |
| 2010/0072254 A1 | 3/2010 | Aranyi et al. | |
| 2010/0147921 A1 | 6/2010 | Olson | |
| 2010/0147922 A1 | 6/2010 | Olson | |
| 2010/0147923 A1 | 6/2010 | D'Agostino et al. | |
| 2010/0236707 A1 | 9/2010 | Olson et al. | |
| 2010/0243708 A1 | 9/2010 | Aranyi et al. | |
| 2010/0243711 A1 | 9/2010 | Olson et al. | |
| 2010/0249805 A1 | 9/2010 | Olson et al. | |
| 2010/0264195 A1 | 10/2010 | Bettuchi | |
| 2010/0282815 A1 | 11/2010 | Bettuchi et al. | |
| 2011/0024476 A1 | 2/2011 | Bettuchi et al. | |
| 2011/0024481 A1 | 2/2011 | Bettuchi et al. | |
| 2011/0036894 A1 | 2/2011 | Bettuchi | |
| 2011/0042442 A1 | 2/2011 | Viola et al. | |
| 2011/0046650 A1 | 2/2011 | Bettuchi | |
| 2011/0057016 A1 | 3/2011 | Bettuchi | |

FOREIGN PATENT DOCUMENTS

| | | | |
|---|---|---|---|
| DE | 199 24 311 | | 11/2000 |
| EP | 0 327 022 | | 8/1989 |
| EP | 0 594 148 | A1 | 4/1994 |
| EP | 0 327 022 | B1 | 4/1995 |
| EP | 0 667 119 | A1 | 8/1995 |
| EP | 1 064 883 | A1 | 1/2001 |
| EP | 1 256 317 | A2 | 11/2002 |
| EP | 1 520 525 | A1 | 4/2005 |
| EP | 1 621 141 | A2 | 2/2006 |
| EP | 1 759 640 | A2 | 3/2007 |
| EP | 2 005 894 | A2 | 12/2008 |
| EP | 2 005 895 | A2 | 12/2008 |
| WO | WO 90/05489 | A1 | 5/1990 |
| WO | WO 97/01989 | A1 | 1/1997 |
| WO | WO 97/13463 | A1 | 4/1997 |
| WO | WO 98/17180 | A1 | 4/1998 |
| WO | WO 99/45849 | A1 | 9/1999 |
| WO | WO 03/082126 | A1 | 10/2003 |
| WO | WO 03/105698 | * | 12/2003 |
| WO | WO 03/105698 | A2 | 12/2003 |
| WO | WO 2006/023578 | A2 | 3/2006 |
| WO | WO 2006/044490 | A2 | 4/2006 |
| WO | WO 2006/083748 | A1 | 8/2006 |
| WO | WO 2008/057281 | A2 | 5/2008 |
| WO | WO 2008/109125 | A1 | 9/2008 |

OTHER PUBLICATIONS

International Search Report corresponding to European Application No. EP 06 00 4598, completed on Jun. 22, 2006; 2 pages.

International Search Report corresponding to European Application No. EP 06 01 6962.0, completed on Jan. 3, 2007 and mailed on Jan. 11, 2007; 10 pages.

International Search Report corresponding to International Application No. PCT/US05/36740, completed on Feb. 20, 2007 and mailed on Mar. 23, 2007; 8 pages.

International Search Report corresponding to International Application No. PCT/US2008/002981, completed on Jun. 9, 2008 and mailed on Jun. 26, 2008; 2 pages.

International Search Report corresponding to European Application No. EP 08 25 1779, completed on Jul. 14, 2008 and mailed on Jul. 23, 2008; 5 pages.

International Search Report corresponding to European Application No. EP 08 25 1989.3, completed on Mar. 11, 2010 and mailed on Mar. 24, 2010; 3 pages.

International Search Report corresponding to European Application No. EP 10 25 0715.9, completed on Jun. 30, 2010 and mailed on Jul. 20, 2010; 3 pages.

International Search Report corresponding to European Application No. EP 05 80 4382.9, completed on Oct. 5, 2010 and mailed on Oct. 12, 2010; 3 pages.

International Search Report corresponding to European Application No. EP 10 25 1437.9, completed on Nov. 22, 2010 and mailed on Dec. 16, 2010; 3 pages.

International Search Report corresponding to European Application No. EP 09 25 2897.5, completed on Feb. 7, 2011 and mailed on Feb. 15, 2011; 3 pages.

International Search Report corresponding to European Application No. EP 10 25 0642.5, completed on Mar. 25, 2011 and mailed on Apr. 4, 2011; 4 pages.

* cited by examiner

ANASTOMOSIS COMPOSITE GASKET

This application is a division of U.S. application Ser. No. 11/080,854 filed Mar. 15, 2005, now U.S. Pat. No. 7,942,890, the entire contents of which is incorporated herein by reference.

BACKGROUND

1. Technical Field

The present disclosure relates to gaskets and, more particularly, to composite gaskets for use in conjunction with stapling devices, for reducing occurrences of leaking, bleeding and/or stricture when anastomosing various body structures.

2. Background of Related Art

Staples have traditionally been used to replace suturing when joining or anastomosing various body structures such as, for example, the bowel or bronchus. The surgical stapling devices employed to apply these staples are generally designed to simultaneously cut and seal an extended segment of tissue in a patient, thus vastly reducing the time and risks of such procedures.

Linear or annular surgical stapling devices are employed by surgeons to sequentially or simultaneously apply one or more linear rows of surgical fasteners, e.g., staples or two-part fasteners, to body tissue for the purpose of joining segments of body tissue together and/or for the creation of anastomoses. Linear surgical stapling devices generally include a pair of jaws or finger-like structures between which body tissue to be joined is placed. When the surgical stapling device is actuated and/or "fired", firing bars move longitudinally and contact staple drive members in one of the jaws, and surgical staples are pushed through the body tissue and into/against an anvil in the opposite jaw thereby crimping the staples closed. A knife blade may be provided to cut between the rows/lines of staples. Examples of such surgical stapling devices are described in U.S. Pat. Nos. 4,354,628, 5,014,899 and 5,040,715, the entirety of each of which is incorporated herein by reference.

In addition to the use of surgical staples, biological tissue adhesives have been developed for tissue repair and the creation of anastomoses. Generally, biological adhesives bond separated tissues together to aid in the healing process and to enhance tissue strength. Such adhesives may be used instead of suturing and stapling, for example, in surgical procedures for the repair of tissue or the creation of anastomoses.

Generally, following the formation of the anastomosis, a separate instrument or device is used to apply biological sealants to the outer surface of the anastomosis. Typically, in a separate step, the biological sealants are applied to the outer surface of the anastomosis by spraying, brushing, swabbing, any combinations thereof, or any other method contemplated by those skilled in the art. The biological sealants act to reduce and/or stop the incidents of leakage from the anastomosis.

The application of a suitable biocompatible adhesive offers many advantages to the patient and the surgeon alike, such as, for example, the possible reduction in the number of staples used, immediate sealing of the tissue being treated, a strengthening of the anastomosis, and a reduction in the occurrence of bleeding from the blood vessels, leakage through the tissue joint, and stricture. Moreover, use of biocompatible adhesives tends to minimize foreign body reaction and scarring.

Annular surgical stapling devices generally include an annular staple cartridge assembly including a plurality of annular rows of staples, typically two, an anvil assembly operatively associated with the annular cartridge assembly, and an annular blade disposed internal of the rows of staples. Examples of such annular surgical stapling devices are described in U.S. Pat. Nos. 5,799,857 and 5,915,616 to Robertson et al., the entirety of each of which is incorporated herein by reference.

In general, an end-to-end anastomosis stapler typically places an array of staples into the approximated sections of a patient's bowels or other tubular organs. The resulting anastomosis contains an inverted section of bowel which contains numerous "B" shaped staples to maintain a secure connection between the approximated sections of bowel.

For most procedures, the use of bare staples, with the staples in direct contact with the patient's tissue, is generally acceptable. The integrity of the tissue will normally serve to prevent the staples from tearing out of the tissue and compromising the sealing before healing has occurred. However, in some surgical operations, surgical supports, e.g., meshes, are employed by surgeons in combination with linear stapling devices to bridge, repair and/or reinforce tissue defects within a patient, especially those occurring in the abdominal wall, chest wall, diaphragm, and other musculo-aponeurotic areas of the body. Examples of suitable surgical supports are disclosed in U.S. Pat. Nos. 3,054,406, 3,124,136, 4,347,847, 4,655,221, 4,838,884 and 5,002,551, the entirety of each of which is incorporated herein by reference.

When the staples are applied in surgical procedures utilizing surgical supports (i.e., reinforcing material), the legs of the staple typically pass from the cartridge jaw through a layer of the surgical support, and through the patient's tissue before encountering the anvil jaw. In an alternative procedure, the legs of the staple typically pass from the cartridge jaw through a first layer of the surgical support, then through the patient's tissue, and finally through a second layer of the surgical support before encountering the anvil jaw. With the staples in place, the stapled tissue is clamped between the layers of the surgical support.

While the surgical supports described above are used in conjunction with linear surgical stapling devices, the need exists for annular support structures for use in conjunction with annular or circular surgical stapling devices, for example, an end-to-end anastomosis stapler such as a Model "EEA™" instrument available from United States Surgical, a Division of Tyco Health-Care Group, LP, Norwalk, Conn. and disclosed in U.S. Pat. No. 5,392,979 to Green et al.

One possible side effect of any end-to-end bowel anastomosis is its tendency to undergo stenosis over time, which can decrease the diameter of the lumen over time. Accordingly, the need exists for an annular surgical structure which operates in conjunction with any end-to-end, annular, or circular anastomosis or stapling device and assists in keeping open the lumen of the anastomosed bowel or other tubular organ over time. There is also a need for a gasket, which would function to seal the anastomosed bowel or other body organ against leakage from between the tissue sections being joined.

A need also exists for an annular support structure which operates in conjunction with any end-to-end, annular or circular stapling device to reduce the trauma suffered by the patient, reduce the instances of leakage, reduce the instances of bleeding, and create a relatively strong bond between adjacent body tissues.

SUMMARY

The present disclosure provides structures and/or gaskets for deposition between adjacent intestinal sections in an anastomosis procedure. The structure possesses at least an inner ring of a first material, and a middle ring of a second material. The first material and the second material include a wound treatment material consisting of at least one of an adhesive, a sealant and/or a medicament. The first material is different from the second material.

The annular structure may be impregnated with the wound treatment material. Desirably, the annular structure is a mesh-like material. It is envisioned that the annular structure may be bio-absorbable.

In one embodiment, the structure further includes an outer ring, wherein the outer ring of the structure includes at least one monomer selected from the group consisting of glycolide, glycolic acid, lactide, lactic acid, p-dioxanone, e-caprolactone, trimethylene carbonate, homopolymers thereof, copolymers thereof, and blends thereof. It is envisioned that the structure further includes an outer ring, wherein the outer ring of the structure includes a knitted mesh of polyglycolic acid yarns in combination with a second material selected from the group consisting of glycolide, lactide, trimethylene carbonate, dioxanone, and combinations thereof.

In another embodiment, the middle ring of the structure includes at least one monomer selected from the group consisting of glycolide, glycolic acid, lactide, lactic acid, p-dioxanone, e-caprolactone, trimethylene carbonate, homopolymers thereof, copolymers thereof, and blends thereof.

In yet another embodiment, wherein the inner ring includes at least one monomer selected from the group consisting of glycolide, glycolic acid, lactide, lactic acid, p-dioxanone, e-caprolactone, trimethylene carbonate, homopolymers thereof, copolymers thereof, and blends thereof.

In an embodiment, the structure may be non-absorbable. It is envisioned that the outer ring of the structure may include at least one non-absorbable material selected from the group consisting of polybuther, polyetherester, polyethylene, polypropylene, nylon, polyethylene terephthalate, polytetrafluoroethylene, polyvinylidene fluoride, stainless steel, and titanium. It is further envisioned that the middle ring of the structure may include at least one non-absorbable material selected from the group consisting of polyethylene, polypropylene, nylon, polyethylene terephthalate, polytetrafluoroethylene, polyvinylidene fluoride, stainless steel, and titanium. It is still further envisioned that the inner ring of the structure may include at least one non-absorbable material selected from the group consisting of polyolefins, nylon, and silk.

In an embodiment, the structure further includes an outer ring including a composite of both non-absorbable and absorbable materials. It is envisioned that the middle ring of the structure may include a composite of both non-absorbable and absorbable materials. It is further envisioned that the inner ring of the structure includes a composite of both non-absorbable and absorbable materials.

In one embodiment, the inner ring of the structure includes at least one gap formed along a length thereof.

The wound treatment material may include at least one adhesive including a hydrogel. The wound treatment material may include at least one sealant selected from the group consisting of fibrin sealants, collagen-based sealants, and synthetic polyethylene glycol-based, hydrogel sealants. It is envisioned that the wound treatment material may include at least one medicament selected from the group consisting of antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, enzymes, and combinations thereof.

In an embodiment, the structure may include a first layer and a second layer. It is envisioned that the first layer of the structure includes a first part of a two-part wound treatment material, and the second layer of the structure includes a second part of the two-part wound treatment material.

The inner ring may include a non-bioabsorbable material and the middle ring may include a bioabsorbable material.

The present disclosure also provides methods for disposing a structure between adjacent intestinal sections. This method involves first providing a circular surgical anastomosis device. The circular surgical anastomosis device possesses an anvil assembly having an anvil member and a first shaft, a tubular body portion having an annular knife operatively disposed therein, and a second shaft disposed radially inward of the annular knife, the first shaft of the anvil assembly being selectively attachable to the second shaft of the tubular body. In carrying out the method of the present disclosure, the anvil assembly is inserted into a first intestinal section, the tubular body portion is inserted into a second intestinal section, and the structure including at least an inner ring and a middle ring is disposed between the first intestinal section and the second intestinal section. The anvil assembly and tubular body portion are then approximated with one another so that the structure is disposed between the first intestinal section and the second intestinal section, and an end portion of the first intestinal section, the structure, and an end portion of the second intestinal section are disposed between the anvil member and the tubular body portion of the circular surgical anastomosis device. The surgical anastomosis device is then fired to sever the portions of the first and second intestinal sections disposed radially inward of the annular knife, and portions of the first and second intestinal sections are placed in contact radially outward of the annular knife against the structure.

The method may further include the step of attaching the first shaft of the anvil assembly to the second shaft of the tubular body portion prior to the step of approximating the anvil assembly to the tubular body portion. According to the method, the structure may include an aperture formed therein. Accordingly, the method may further include the step of inserting one of the first shaft of the anvil assembly and the second shaft of the tubular body portion into the aperture of the structure prior to the step of attaching the first shaft of the anvil assembly to the second shaft of the tubular body portion.

It is envisioned that the structure may be bio-absorbable or non-absorbable. Desirably, the structure includes a composite of at least one bio-absorbable material in combination with at least one non-absorbable material. It is envisioned that the structure may be a mesh-like material.

It is envisioned that the tubular body portion may carry a plurality of surgical staples in a circular configuration. The surgical staples are disposed radially outward of the annular knife, wherein upon firing of the anastomosis device, the plurality of staples penetrate a first interstitial section, the structure and then a second interstitial section. The step of firing the surgical anastomosis device desirably includes driving the plurality of staples from the tubular body portion through the second intestinal section, through the structure, through the first intestinal section, and against the anvil member.

It is envisioned that the structure may include a first layer and a second layer. Desirably, the first layer of the structure includes a first part of a two-part wound treatment material, and the second layer of the structure includes a second part of the two-part wound treatment material.

The structure may include a first part of a two-part wound treatment material, and the method may further include the step of applying a second part of the two-part wound treatment material to the structure.

The structure may include a first part of a two-part adhesive, and wherein the step of deploying the adhesive material includes applying a second part of the two-part adhesive to the support structure prior to the step of approximating.

It is envisioned that the middle ring includes the bio-absorbable material and the inner ring includes the non-bio-absorbable material. The annular knife may then sever the non-absorbable material from the bio-absorbable material. The knife may sever the structure so that a portion of the non-absorbable material remains between the first and second intestinal sections.

It is envisioned that the non-absorbable material may be arranged so as to be passed from the body upon at least partial absorption of the bio-absorbable material.

BRIEF DESCRIPTION OF DRAWINGS

The accompanying drawings, which are incorporated in and constitute a part of this specification, illustrate embodiments of the disclosure and, together with a general description of the disclosure given above and the detailed description of the embodiments given below, serve to explain the principles of the disclosure, wherein.

DETAILED DESCRIPTION OF EMBODIMENTS

Embodiments of the presently disclosed circular anastomosis structures, also referred to herein as circular anastomosis gaskets, will now be described in detail with reference to the drawing figures wherein like reference numerals identify similar or identical elements. As used herein and as is traditional, the term "distal" refers to that portion which is furthest from the user while the term "proximal" refers to that portion which is closest to the user.

Figure 1:
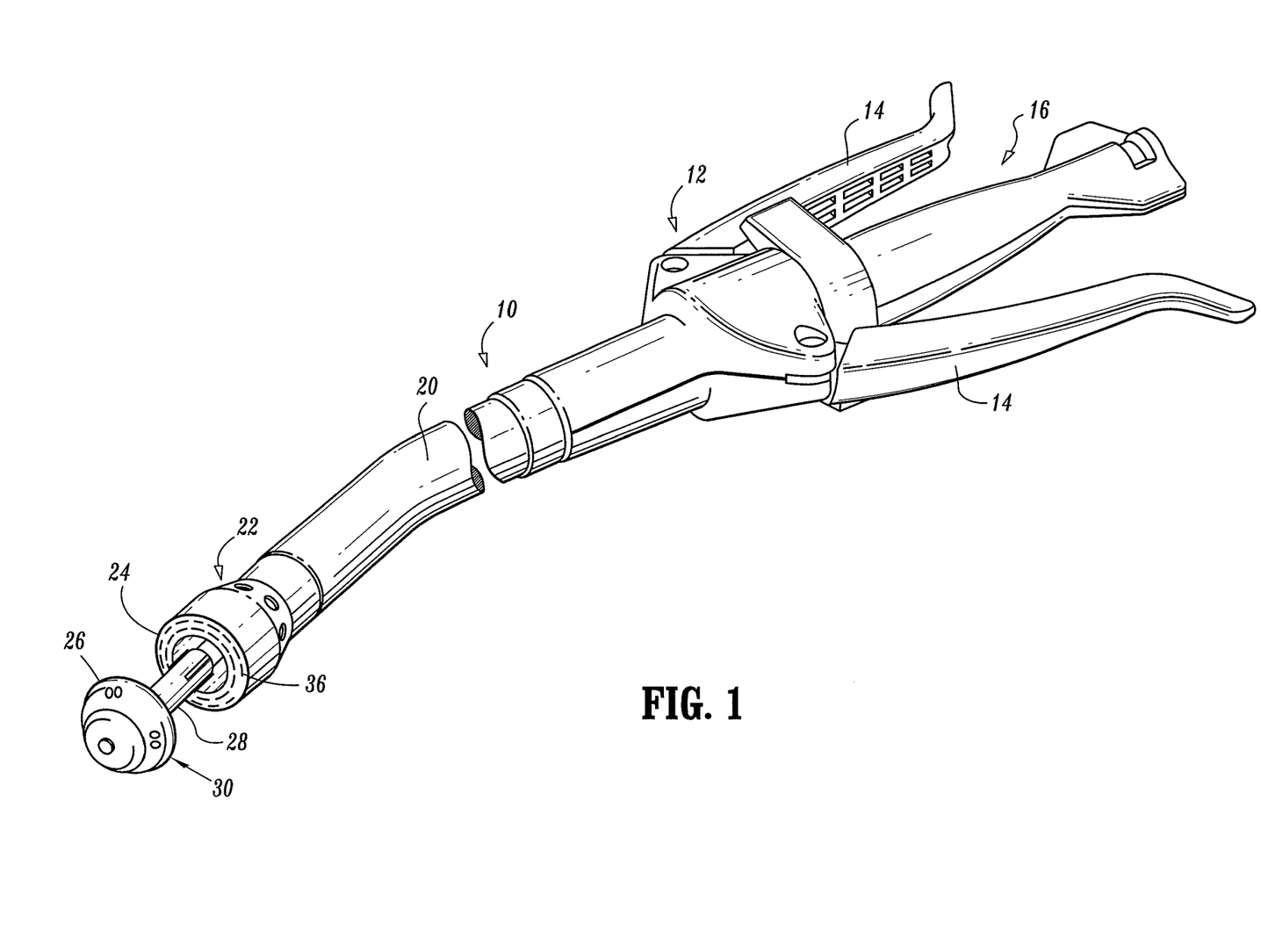
FIG. 1 is a perspective view of an exemplary annular surgical stapling device.

Referring initially to FIG. 1, an annular surgical stapling device, for use with the circular anastomosis structures disclosed herein, is generally designated as 10. Surgical stapling device 10 includes a handle assembly 12 having at least one pivotable actuating handle member 14, and an advancing member 16. Extending from handle member 12, there is provided a tubular body portion 20 which may be constructed so as to have a curved shape along its length. Body portion 20 terminates in a staple cartridge assembly 22 which includes a pair of annular arrays of staple receiving slots 36 having a staple (not shown) disposed in each one of staple receiving slots 36. Positioned distally of staple cartridge assembly 22 there is provided an anvil assembly 30 including an anvil member 26 and a shaft 28 operatively associated therewith for removably connecting anvil assembly 30 to a distal end portion of stapling device 10.

Staple cartridge assembly 22 may be fixedly connected to the distal end of tubular body portion 20 or may be configured to concentrically fit within the distal end of tubular body portion 20. Typically, staple cartridge assembly 22 includes a staple pusher (not shown) including a proximal portion having a generally frusto-conical shape and a distal portion defining two concentric rings of peripherally spaced fingers (not shown), each one of which is received within a respective staple receiving slot 36.

Typically, a knife (not shown), substantially in the form of an open cup with the rim thereof defining a knife edge, is disposed within staple cartridge assembly 22 and mounted to a distal surface of a staple pusher (not shown). The knife edge is disposed radially inward of the pair of annular arrays of staples. Accordingly, in use, as the staple pusher is advanced, the knife is also advanced axially outward.

Reference may be made to U.S. Pat. No. 5,915,616 to Viola et al., the entire contents of which are incorporated herein by reference, for a detailed discussion of annular stapling device 10.

Figure 2:
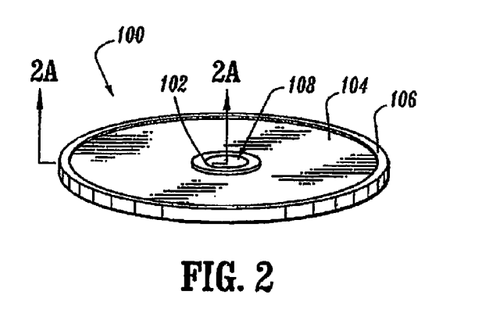
FIG. 2 is a perspective view of a circular anastomosis structure in accordance with an embodiment of the present disclosure, for use with the annular surgical stapling device of FIG. 1.
Figure 2A:
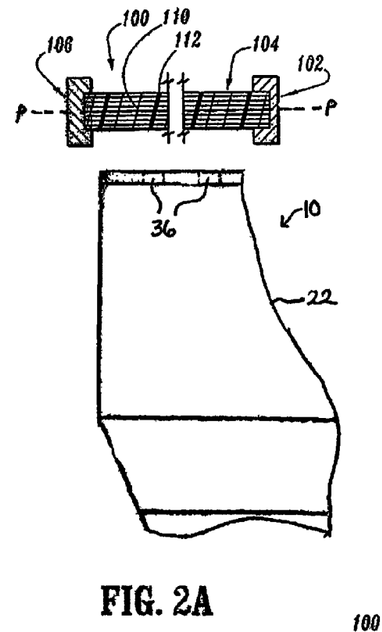
FIG. 2A is a cross-sectional view of the circular anastomosis structure of FIG. 2, as taken through 2A-2A of FIG. 2, shown in spaced relation to the staple cartridge assembly of the surgical stapling device of FIG. 1.
Figure 3:
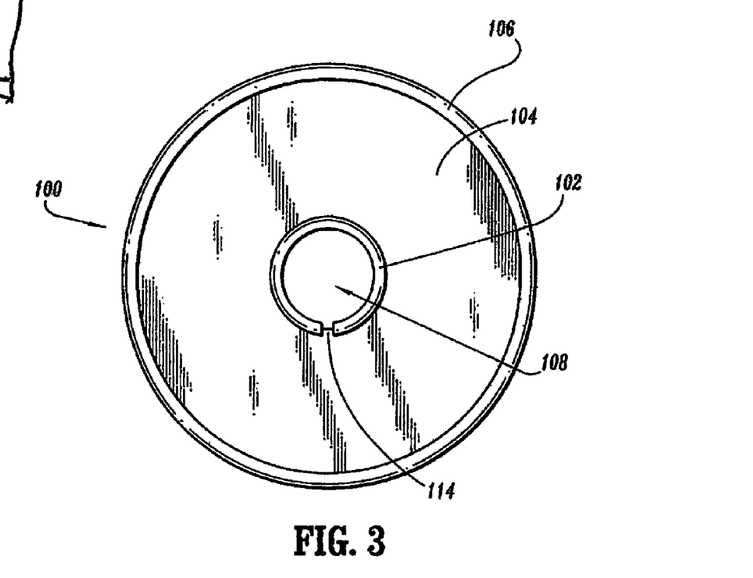
FIG. 3 is a top view of a circular anastomosis structure in accordance with another embodiment of the present disclosure, for use with the annular surgical stapling device of FIG. 1.

Turning now to FIGS. 2, 2A, and 3, an anastomosis structure, in accordance with an embodiment of the present disclosure, is generally designated as structure 100. Structure 100 includes an inner ring 102, a middle ring 104, and an outer ring 106 lying along a common plane "P". A substantially centrally located aperture 108, defined by the inner circumference of inner ring 102 is formed through structure 100.

In one embodiment, structure 100 is sized such that when structure 100 is operatively associated with stapling device 10, as will be described in greater detail below, outer ring 106 extends radially beyond staple retaining pockets 36 (see FIG. 1 and FIG. 2A) of staple cartridge assembly 22. Additionally, aperture 108 of structure 100 is sized to at least receive shaft 28 of anvil assembly 30 therethrough. In another embodiment, the distance between outer ring 106 and inner ring 102 is substantially equal to a width of a tissue contacting surface 24 (see FIG. 1 and FIG. 2A) of staple cartridge assembly 22.

As seen in FIG. 3, circular anastomosis structure 100 includes at least two concentric rings. Where a three ring structure is utilized, as shown in FIGS. 2 and 3, structure 100 includes an inner ring 102, a middle ring 104 and an outer ring 106. Where a two ring structure is utilized (not shown), structure 100 includes a middle ring 104 and an outer ring 106. In this embodiment, inner ring 102 is missing and/or is otherwise optional.

It is contemplated that inner ring 102 may, in some embodiments, be made from non-absorbable materials including, but not limited to, both synthetic and natural materials, including polyolefins such as polypropylenes, nylon, and silk. Inner ring 102 may also be made of absorbable materials, including homopolymers, copolymers or blends obtained from one or more monomers selected from the group consisting of glycolide, glycolic acid, lactide, lactic acid, p-dioxanone, e-caprolactone and trimethylene carbonate. In some embodiments, inner ring 102 may be a composite of both non-absorbable and absorbable materials.

As seen in FIG. 3, in one embodiment the inner ring may 102 have one or more gaps 114 formed therein and/or therealong to help facilitate passage of inner ring 108 out of the patients' body and to help facilitate introduction of shaft 28 of anvil assembly 30 into aperture 108.

It is contemplated that middle ring 104 of structure 100 may be fabricated from or include a surgical grade, biocompatible, non-absorbable (i.e., permanent) or absorbable (i.e., non-permanent) mesh or material desirably impregnated with an adhesive, sealant and/or other medicament. As used herein, "mesh" includes woven, knitted and braided materials. In addition, non-woven materials such as felts may be used. For example, middle ring 104 may be fabricated from "TEFLON", which is a registered trademark owned by DuPont de Nemours & Co. It is further contemplated that middle ring 104 may be fabricated from a biocompatible polymeric foam, felt, polytetrafluoroethylene (ePTFE), gelatin, fabric or the like, or any other biocompatible material.

Non-absorbable materials used for middle ring 104 include, but are not limited to, those that are fabricated from such polymers as polybutester, polyetherester, polyethylene, polypropylene, nylon, polyethylene terephthalate, polytetrafluoroethylene, polyvinylidene fluoride, and the like. Further non-absorbable materials which may be utilized include, but are not limited to, stainless steel, titanium and the like.

Bio-absorbable materials used for middle ring 104 of structure 100 include, but are not limited to, those fabricated from homopolymers, copolymers or blends obtained from one or more monomers selected from the group consisting of glycolide, glycolic acid, lactide, lactic acid, p-dioxanone, e-caprolactone and trimethylene carbonate. Other bio-absorbable materials include, but are not limited to, polyglycolic acid (PGA) and polylactic acid (PLA). In one embodiment, middle ring 104 may be fabricated from bio-absorbable felt, ePTFE, gelatin or any other bio-absorbable materials. In one particularly useful embodiment, polyglycolic acid (PGA) yams may be used as the middle ring 104 of the circular anastomosis structure of the present disclosure. Suitable yarns include those sold in a mesh form as DEXON™ mesh by United States Surgical, a Division of Tyco Health-Care Group, LP, Norwalk, Conn.

In one particularly useful embodiment, as seen in FIG. 2A, middle ring 104 may be made from a composite material made from a majority 110 of an absorbable yarn with a minority 112 of non-absorbable yarn, such as silk, cotton, nylon, polypropylene, polyester, polyethylene terephtialate, and the like. In some cases, it may be advantageous to include a minor portion of a non-absorbable yarn to increase tissue growth by enhancing tissue reactivity. While materials such as silk, cotton and nylon are classified by the FDA as non-absorbable materials, they will eventually break-down in the body, at a much slower rate than absorbable materials.

As with inner ring 102, in some embodiments middle ring 104 may be a composite of both non-absorbable and absorbable materials.

Outer ring 106 may similarly be made of non-absorbable or absorbable materials described above for use in forming middle ring 104 or inner ring 102. In some embodiments, outer ring 106 may also be made from a composite of absorbable materials combining a knitted mesh such as DEXON™ mesh with an absorbable synthetic wax or synthetic sealant. For example, this absorbable material can be made from short-chain polymer(s) such as glycolide, lactide, trimethylene carbonate, dioxanone or the like, and any combinations thereof.

In a further embodiment, the structure has a middle ring and an inner ring and incorporates at least two different materials. The inner ring is formed from a non-bioabsorbable material, whereas the middle ring is formed from bio-absorbable materials and is preferably a compressible material arranged to be compressed between adjacent tissue sections so as to form a seal. The inner ring is desirably arranged so as to be at least partially removed by the circular knife of the stapling device and/or passed from the body.

As noted above, in some embodiments a minor portion of a non-absorbable material may also be incorporated into inner ring 102, outer ring 106, or both.

Figure 4:
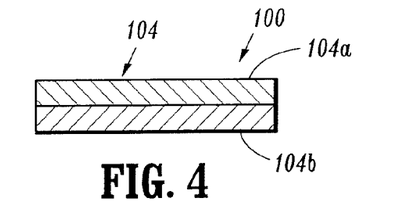
FIG. 4 is a cross-sectional view of a circular anastomosis structure in accordance with an alternate embodiment of the present disclosure, as taken through the middle ring of FIG. 2, for use with the annular surgical stapling device of FIG. 1.
Figure 5:
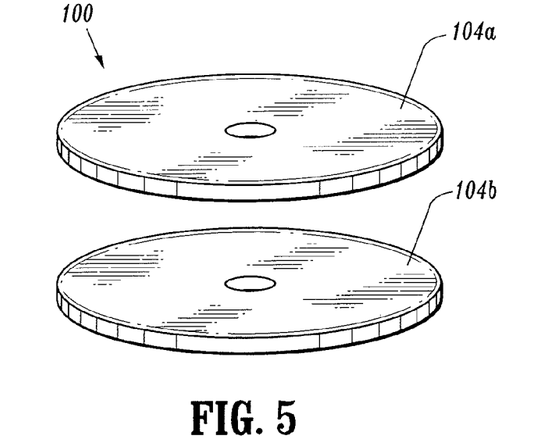
FIG. 5 is a perspective view of a circular anastomosis structure in accordance with another embodiment of the present disclosure, for use with the annular surgical stapling device of FIG. 1.

In yet another embodiment, as seen in FIGS. 4 and 5, middle ring 104 can be made from a sandwich of composite materials including an upper layer 104a and a lower layer 104b. Desirably, layers 104a, 104b may be a knitted mesh made from both absorbable and non-absorbable yarns and include a sealant as a middle layer to secure layers 104a, 104b to one another. Sealants which may be utilized to adhere the upper and lower layers 104a, 104b of the middle ring are known to those skilled in the art and include, but are not limited to, hydrogels, fibrin-based sealants, thrombin-based sealants, collagen-based sealants, and synthetic polymer sealants including those based on polyalkylene oxides such as polyethylene glycol, polydioxanones, polylactides, polyglycolides, polycaprolactones. In one particularly useful embodiment, the sealant utilized to adhere the upper and lower layers 104a, 104b of middle ring 104 is an absorbable sealant which swells after contact with water, e.g., a hydrogel, which is analogous to a "foam in place" sealant.

In yet another embodiment, the multi-layer composite mesh utilized to form the middle ring 104 may be pre-impregnated (i.e., coated) with the swelling absorbable sealant.

In one embodiment, middle ring 104 of structure 100 may be fabricated from a bio-absorbable material which is desirably impregnated with an adhesive, sealant, and/or other medicament (i.e., wound treatment material). Accordingly, in use, the sealant component of structure 100 functions to retard any bleeding which may occur from the tissue, the adhesive component of structure 100 functions to help secure the approximated tissue together, and the bio-absorbability of structure 100 allows for at least a portion of structure 100 to be absorbed into the body after a predetermined amount of time. For example, structure 100 may remain in place in the body for approximately 2-3 weeks in order for the anastomosis to sufficiently heal prior to structure 100 being absorbed into the body.

Where utilized, the adhesive should be a biocompatible adhesive including, but not limited to, adhesives which cure upon tissue contact, which cure upon exposure to ultraviolet (UV) light, which are two-part systems kept isolated from one another and cure upon coming into contact with one another, which are pressure sensitive, which are any combinations thereof, or any other known suitable adhesive. In one embodiment, it is contemplated that an adhesive having a cure time of from about 10 to about 15 seconds may be used. In another embodiment, it is contemplated that an adhesive having a cure time of about 30 seconds may be used.

It is envisioned that middle ring 104 of structure 100 may be impregnated with a pre-cured adhesive or sealant. The pre-cured sealant or adhesive will react with the moisture and/or heat of the body tissue to thereby activate the sealing and/or adhesive properties of the sealant or adhesive. Thus, in one embodiment the pre-cured sealant or adhesive may be a hydrogel or the like.

It is envisioned that the adhesive may be utilized alone or combined with one or more other wound treatment materials. Other surgically biocompatible wound treatment materials which may be employed in or applied by surgical instruments, especially surgical staplers utilized to repair tissue and create anastomosis with the anastomosis composite structure herein, include adhesives whose function is to attach or hold organs, tissues or structures; sealants to prevent fluid leakage; hemostats to halt or prevent bleeding; and medicaments.

Examples of additional adhesives which can be employed include protein derived, aldehyde-based adhesive materials, for example, the commercially available albumin/glutaraldehyde materials sold under the trade designation BioGlue™ by Cryolife, Inc., and cyanoacrylate-based materials sold under the trade designations Indermil™ and Derma Bond™ by Tyco Healthcare Group, LP and Ethicon Endosurgery, Inc., respectively. Examples of sealants which can be employed include fibrin sealants and collagen-based and synthetic polymer-based tissue sealants. Examples of commercially available sealants are synthetic polyethylene glycol-based, hydrogel materials sold under the trade designation CoSeal™ by Cohesion Technologies and Baxter International, Inc.

Examples of hemostat materials which can be employed include fibrin-based, collagen-based oxidized regenerated cellulose-based, and gelatin-based topical hemostats. Examples of commercially available hemostat materials are fibrinogen-thrombin combination materials sold under the trade designations CoStasis™ by Tyco Healthcare Group, LP, and Tisseel™ sold by Baxter International, Inc. Hemostats herein also include astringents, e.g., aluminum sulfate, and coagulants.

The term "medicament", as used herein, is used in its broadest sense and includes any substance or mixture of substances that have clinical use. Consequently, medicaments may or may not have pharmacological activity per se, e.g., a dye. Alternatively a medicament could be any agent which provides a therapeutic or prophylactic effect, a compound that affects or participates in tissue growth, cell growth, cell differentiation, a compound that may be able to invoke a biological action such as an immune response, or could play any other role in one or more biological processes.

Examples of classes of medicaments which may be utilized in accordance with the present disclosure include antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of medicaments may be used.

Suitable antimicrobial agents which may be included as a medicament in the circular anastomosis structure of the present disclosure include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a medicament in the circular anastomosis structure of the present disclosure.

Other medicaments which may be included in the circular anastomosis structure of the present disclosure include: local anesthetics; non-steroidal antifertility agents; parasympathomimetic agents; psychotherapeutic agents; tranquilizers; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g. oxybutynin); bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable medicaments which may be included in the circular anastomosis structure of the present disclosure include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons (β-IFN, (a-IFN and ?-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; and ribozymes.

A single medicament may be utilized in the circular anastomosis structure of the present disclosure or, in alternate embodiments, any combination of medicaments may be utilized in the circular anastomosis structure of the present disclosure.

The medicament may be disposed on a surface of structure 100 or impregnated into structure 100. The medicament may include one or more medically and/or surgically useful substances such as drugs, enzymes, growth factors, peptides, proteins, dyes, diagnostic agents or hemostatic agents, or any other pharmaceutical used in the prevention of stenosis.

In one embodiment, it is contemplated that middle ring 104 of structure 100 may be impregnated with a first component of a two-part adhesive and that the staples, retained in staple receiving slots 36 of staple cartridge assembly 22, may be coated with a second component (e.g., a reactant) of the two-part adhesive. In this manner, the first component of the adhesive is activated when the staples penetrate and capture middle ring 104 of structure 100 during the firing sequence of surgical stapling device 10, and the two components of the adhesive contact one another.

As seen in FIG. 3, structure 100 may include a single layered middle ring 104 including a homogeneous array of bio-absorbable or non-absorbable materials or a heterogeneous array or bio-absorbable and/or non-absorbable materials.

As seen in FIGS. 4 and 5 and as discussed above, structure 100 may include at least a dual layered middle ring 104 as indicated by first layer, film or wafer 104a and second layer, film or wafer 104b. In this embodiment, each layer 104a, 104b may include a homogeneous or heterogeneous array of bio-absorbable and/or non-absorbable materials. It is envisioned that each layer 104a, 104b may be separated from one another, as seen in FIG. 5, prior to the surgical procedure.

As will be described in greater detail below, first layer 104a of structure 100 may be placed against a surface of a first tissue to be anastomosed, in juxtaposition to a second tissue to be anastomosed, and second layer 104b of structure 100 may be placed against a surface of the second tissue to be anastomosed, in juxtaposition to the first tissue to be anastomosed. In this manner, as the first and second tissues are brought into contact with one another, first and second layers 104a, 104b of structure 100 are brought into contact with one another and allowed to mix and/or react. For example, first layer 104a of structure 100 may include a first component of a two-part adhesive or sealant while second layer 104b of structure 100 may include a second component of the two-part adhesive or sealant. Accordingly, in use, when first layer 104a and second layer 104b come into contact with one another, the first and second components of the two-part adhesive or sealant will also come into contact and mix thereby forming the adhesive or sealant.

First and second layers 104a and 104b may be fabricated as bio-absorbable film-like membranes which activate upon contact with one another and/or contact with a fluid (e.g., water, saline, blood, an activating fluid, etc.). It is envisioned that a break-away or tear-away divider or barrier (not shown) may be positioned between first and second layers 104a, 104b in order to prevent accidental and/or premature contact between first and second layers 104a and 104b. It is further envisioned that each first and second layer 104a and 104b may include a liner (not shown) removably disposed on at least one of a top or bottom surface thereof. In any of these embodiments, prior to contact of first and second layers 104a and 104b with one another, the divider and/or liners must be removed in order for activation of the adhesive to occur.

It is further envisioned that middle ring 104 of structure 100 may be impregnated with a pressure sensitive adhesive which is activated when the adjacent layers of tissue are approximated. Suitable pressure sensitive adhesives are known to those skilled in the art and include, for example, acrylate polymers, methacrylate polymers. In some embodiments, the pressure sensitive adhesive may be an alkyl methacrylate including, but not limited to, alkyl methacrylates containing 1 to about 10 carbon atoms in the alkyl group. Representative examples of suitable alkyl methacrylates include methyl methacrylate, n-butyl methacrylate, n-pentyl methacrylate, n-hexyl methacrylate, isoheptyl methacrylate, cyclohexyl methacrylate, n-nonyl methacrylate, n-decyl methacrylate, isohexyl methacrylate, 2-ethyloctyl methacrylate, isooctyl methacrylate, isobornyl methacrylate, 2-ethylhexyl methacrylate, and mixtures and combinations of the foregoing. Typically, the alkyl methacrylate may be isooctyl methacrylate, butyl methacrylate, 2-ethylhexyl methacrylate, cyclohexyl methacrylate, isobornyl methacrylate, and/or methyl methacrylate.

In some embodiments, the pressure sensitive adhesive may be a copolymer including an alkyl methacrylate described above copolymerized with one or more methacrylate monomers having at least one functional group selected from the grouping consisting of carboxylic acid, carboxylic acid ester, hydroxyl, anydride, epoxy, thiol, isocyanate, sulfonamide, urea, carbamate, carboxamide, amine, ammonium, oxy, oxo, nitro, nitrogen, sulfur, phosphate, phosponate, cyano, combinations of these, and the like. Representative examples of specific materials that can be used singly or in combination as the methacrylate monomer having at least one functional group include methacrylic acid, maleic acid, vinyl acetate, a hydroxyalkyl methacrylate containing about 2 to about 4 carbon atoms in the hydroxyalkyl group, methacrylamide, an alkyl substituted methacrylamide having 1 to about 8 carbon atoms in the alkyl group, diacetone methacrylamide, a dialkyl methacrylamide independently having 1 or 2 carbon atoms in each alkyl group, N-vinyl-N-methyl acetamide, N-vinyl lactams, N-vinyl valerolactam, N-vinyl caprolactam, N-vinyl-2-pyrrolidone, glycidyl methacrylate, alkoxy methacrylate containing 1 to 4 carbon atoms in the alkoxy group, 2-ethoxyethyl methacrylate, 2,2-ethoxyethoxyethyl methacrylate, furfuryl methacrylate, tetrahydrofurfuryl methacrylate, propylene glycol monomethacrylate, polyethylene glycol methacrylate, polyethylene glycol methyl ether methacrylate, polyethylene oxide methyl ether methacrylate, di(lower)alkylaminopropyl methacrylamide (wherein lower means the alkyl moiety has 1 to 4 carbon atoms), methacrylonitrile, combinations of these, and the like. Typically, the copolymerizable monomer having at least one functional group include may be hydroxyethyl acrylate, hydroxyethyl methacrylate, acrylamide, glyceryl acrylate, N,N-dimethyl acrylamide, 2-ethoxyethyl acrylate, 2,2-ethoxyethoxyethyl acrylate, tetrahydrofurfuryl acrylate, vinyl acetate, and/or acrylic acid. Any of the aforementioned alkyl groups may be linear, branched or cyclic.

Figure 6:
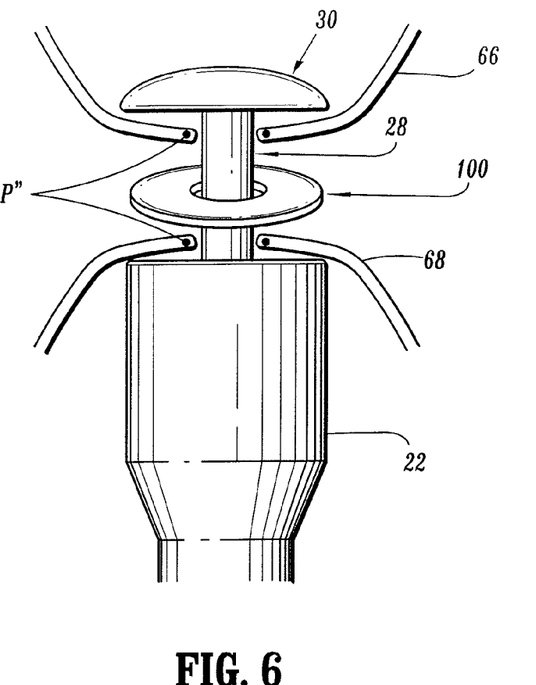
FIG. 6 is a side elevational view of the circular anastomosis structure of FIG. 5, illustrated in position on the annular surgical stapling device of FIG. 1.

As seen in FIG. 6, in use structure 100 may be placed such that aperture 108 receives shaft 28 of anvil assembly 30 therethrough and is at least substantially axially aligned with staple receiving slots 36 (see FIG. 1) of cartridge assembly 22.

Figure 7:
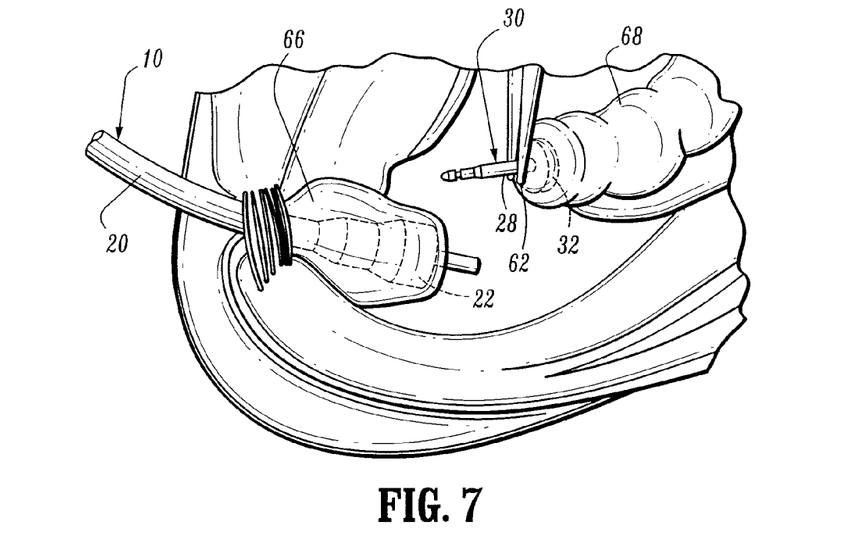
FIG. 7 is a perspective view of the intestinal area of a patient, illustrating a method of positioning the circular anastomosis structure of FIGS. 2, 3 and 4 on the anvil rod of the annular stapling device of FIG. 1.
Figure 8:
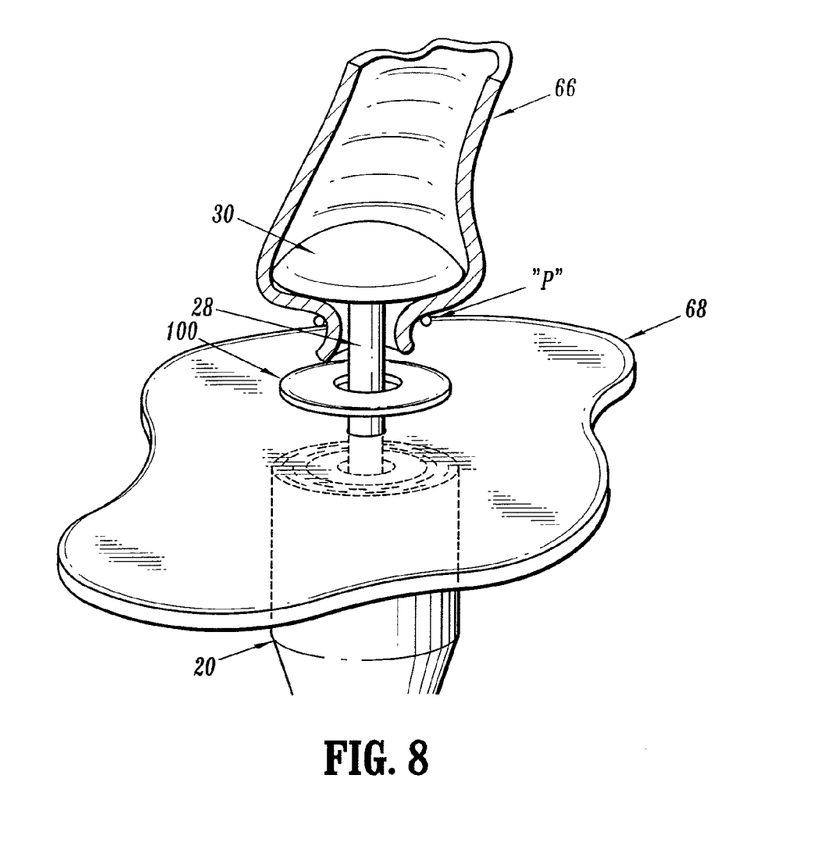
FIG. 8 is a schematic perspective view of the intestinal area of FIG. 7, illustrating the anvil rod mounted to the annular stapling device and having the circular anastomosis structure of FIGS. 2, 3 and 4 disposed therebetween.

Turning now to FIGS. 7 and 8, there is illustrated the use of surgical stapling device 10 and detachable anvil assembly 30 in an anastomosis procedure to effect joining of intestinal sections 66 and 68. The anastomosis procedure is typically performed using minimally invasive surgical techniques including laparoscopic means and instrumentation. At the point in the procedure shown in FIG. 7, a diseased intestinal section has been previously removed, anvil assembly 30 has been applied to the operative site either through a surgical incision or transanally and positioned within intestinal section 68, and tubular body portion 20 of surgical stapling device 10 has been inserted transanally into intestinal section 66. Intestinal sections 66 and 68 are also shown temporarily secured about their respective components (e.g., shaft 28 of anvil assembly 30, and the distal end of tubular body portion 20) by conventional means such as a purse string suture "P" (see FIG. 8).

According to one method, as seen in FIG. 8, if desired or if the surgical procedure requires, circular anastomosis structure 100 may be placed onto shaft 28 of anvil assembly 30 prior to the coupling of anvil assembly 30 to the distal end of tubular body portion 20. Following positioning of structure 100 onto shaft 28 of anvil assembly 30, the surgeon maneuvers anvil assembly 30 until the proximal end of shaft 28 is inserted into the distal end of tubular body portion 20 of surgical stapling device 10, wherein the mounting structure (not shown) within the distal end of tubular body portion 20 engages shaft 28 to effect the mounting.

Thereafter, anvil assembly 30 and tubular body portion 20 are approximated to approximate intestinal sections 66, 68 and capture circular anastomosis structure 100 therebetween. Surgical stapling device 10 is then fired thereby stapling intestinal sections 66, 68 to one another and cutting the portion of tissue and structure 100 disposed radially inward of the knife, to complete the anastomosis. Structure 100 may then release the adhesive impregnated therein to thereby adhere intestinal sections 66 and 68 to one another.

In the event that a structure 100 having a first and second layer 104*a* and 104*b*, each including one part of a two-part adhesive composition, is used, it is envisioned that first and second layers 104*a* and 104*b* are maintained separated and/or isolated from one another until approximation and firing of the surgical stapling device is to occur. Accordingly, in use, one of first and second layers 104*a*, 104*b* may be placed on shaft 28 of anvil assembly 30, against the surface of intestinal section 68, while the other of first and second layers 104*a*, 104*b* is placed against the surface of intestinal section 66. It is envisioned that pins (not shown) may extend distally from the distal end of tubular body portion 20 and penetrate through intestinal section 66. In this manner, the other of first and second layers 104*a*, 104*b* may be pinned onto the pins extending through intestinal section 66.

Alternatively, if a structure 100, having a first and second layer 104*a* and 104*b*, each including one part of a two-part adhesive composition, is used, it is envisioned that that each layer 104*a*, 104*b* may be provided with a tear-away or removable liner for maintaining first and second layers 104*a*, 104*b* separated and/or isolated from one another. Accordingly, both first and second layers 104*a*, 104*b* may be placed on shaft 28 of anvil assembly 30.

If a structure 100, having a first and second layer 104*a*, 104*b*, each including one part of a two-part adhesive composition, is used, the adhesive composition may be activated upon first and second layers 104*a*, 104*b* coming into contact with one another.

From the foregoing, it will be appreciated that the circular anastomosis structures of the present disclosure function to strengthen the anastomosis and reduce the occurrence of bleeding, leaking and stricture. It is also to be appreciated that the circular anastomosis structures of the present disclosure may be utilized in a number of other applications and is not limited solely to bowel or bronchus anastomosis.

Each circular anastomosis structure described above is constructed to enhance the formation of an anastomosis at the target surgical site. In some embodiments, the circular anastomosis structure may also be used to deliver an adhesive to the surgical site. The amount of adhesive to be delivered is site specific. Accordingly, different sized (e.g., different thickness or different volume) circular anastomosis structures are contemplated for retaining a different volume or quantity of adhesive therein. In this manner, depending on the particular need and the particular surgical procedure, the surgeon may select a circular anastomosis structure containing the needed and/or desired volume or quantity of adhesive therein.

While several particular forms of the circular anastomosis structures have been illustrated and described, it will also be apparent that various modifications can be made without departing from the spirit and scope of the present disclosure. For example, it is envisioned and within the scope of the present disclosure for an ultraviolet light activated adhesive to be used in connection with any of the circular anastomosis structures described above. In use, either prior to or following firing of surgical stapling device 10, the circular anastomosis structure is irradiated with UV light to thereby activate the adhesive.

It is further contemplated that each of the circular anastomosis structures described herein may be used with an annular surgical anastomosing device, not including any staples for securing tissue together, which is capable of approximating, adhering and cutting tissue.

Thus, it should be understood that various changes in form, detail and application of the circular anastomosis structures of the present disclosure may be made without departing from the spirit and scope of the present disclosure.

What is claimed is:

1. A method of forming an anastomosis between intestinal tissue sections, comprising the steps of:

providing a circular surgical anastomosis device, the circular surgical anastomosis device including: an anvil assembly having an anvil member; and a tubular body portion having an annular knife operatively disposed therein and a shaft disposed radially inward of the annular knife, the anvil assembly being attached to the shaft of the tubular body;

inserting the anvil assembly into a first intestinal section;

inserting the tubular body portion into a second intestinal section;

disposing a structure, including at least a first ring of a first material, a second ring of a second material, and a third ring between the first intestinal section and the second intestinal section, the first ring comprising a disk having an aperture and the second ring comprising a disk having an aperture, the second ring having an outer perimeter, wherein the outer perimeter of the second ring is directly attached to the first ring and disposed within the aperture of the first ring, and the third ring radially extending outward from the first ring and beyond staple retaining slots of the tubular body portion, the structure possessing a wound treatment material consisting of at least one of an adhesive and a sealant; and firing staples through the intestinal tissue sections and through the structure.

2. The method according to claim 1, further comprising:

approximating the anvil assembly and tubular body portion with one another so that an end portion of the first intestinal section, the structure, and an end portion of the second intestinal section are disposed between the anvil member and the tubular body portion, the structure being disposed between the first intestinal section and the second intestinal section; and firing the surgical anastomosis device to sever the portions of the first and second intestinal sections disposed radially inward of the annular knife, and to touch the portions of the first and second intestinal sections radially outward of the annular knife against the structure.

3. The method according to claim 1, further including the step of inserting the shaft into the aperture of the second ring of the structure.

4. The method according to claim 3, wherein the anvil assembly has a shaft that is selectively attachable to the shaft of the tubular body portion and further comprising attaching the shaft of the anvil assembly to the shaft of the tubular body portion after inserting the shaft of the tubular body portion into the aperture of the second ring.

5. The method according to claim 1, wherein the structure is bio-absorbable.

6. The method according to claim 1, wherein the structure is non-absorbable.

7. The method according to claim 1, wherein the structure comprises a composite of at least one bio-absorbable material in combination with at least one non-absorbable material.

8. The method according to claim 1, wherein the structure is a mesh-like material.

9. The method according to claim 1, wherein the tubular body portion carries a plurality of surgical staples in a circular configuration, the surgical staples being disposed radially outward of the annular knife, whereupon firing of the anastomosis device, the plurality of staples penetrate the first intestinal section, the structure and then the second intestinal section.

10. The method according to claim 1, wherein the structure includes a first, upper layer and a second, lower layer.

11. The method according to claim 1, wherein the first ring comprises the bio-absorbable material and the second ring comprises the non-bio-absorbable material.

12. The method according to claim 11, wherein the annular knife severs the non-absorbable material from the bio-absorbable material.

13. The method of claim 1, wherein the first material of the structure is different from the second material.

14. The method of claim 1, wherein the first and second rings of the structure are co-planar.

15. The method of claim 1, wherein the first ring is disposed about the outer perimeter of the second ring.

* * * * *